United States Patent
Zeller et al.

(10) Patent No.: US 11,136,289 B2
(45) Date of Patent: *Oct. 5, 2021

(54) PROCESS AND INTERMEDIATE

(71) Applicant: SYNGENTA PARTICIPATIONS AG, Basel (CH)

(72) Inventors: Martin Zeller, Münchwilen (CH); Nicolas Fedou, Münchwilen (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,231

(22) Filed: May 27, 2020

(65) Prior Publication Data

US 2020/0283374 A1 Sep. 10, 2020

Related U.S. Application Data

(63) Continuation of application No. 16/319,304, filed as application No. PCT/EP2017/068345 on Jul. 20, 2017, now Pat. No. 10,759,742.

(30) Foreign Application Priority Data

Jul. 22, 2016 (EP) ..................... 16180827

(51) Int. Cl.
| | | |
|---|---|---|
| *C07C 255/35* | (2006.01) | |
| *C07C 51/08* | (2006.01) | |
| *C07C 53/134* | (2006.01) | |
| *C07C 255/33* | (2006.01) | |
| *C07C 253/30* | (2006.01) | |
| *B01J 31/24* | (2006.01) | |

(52) U.S. Cl.
CPC ............ *C07C 255/35* (2013.01); *C07C 51/08* (2013.01); *C07C 53/134* (2013.01); *C07C 253/30* (2013.01); *C07C 255/33* (2013.01); *B01J 31/24* (2013.01); *B01J 2231/44* (2013.01); *B01J 2531/824* (2013.01)

(58) Field of Classification Search
CPC .................................................. C07C 255/35
See application file for complete search history.

(56) References Cited

U.S. PATENT DOCUMENTS

| | | | | |
|---|---|---|---|---|
| 7,268,247 B2* | 9/2007 | Zeller | ............... | C07C 253/30 558/357 |
| 2004/0092750 A1* | 5/2004 | Hasegawa | ............ | C07D 209/08 548/510 |
| 2010/0261934 A1* | 10/2010 | Fischer | ................ | C07D 207/36 562/496 |
| 2016/0159799 A1 | 6/2016 | Godineau et al. | | |

FOREIGN PATENT DOCUMENTS

| | | |
|---|---|---|
| EP | 1367050 A1 | 12/2003 |
| WO | 9947525 A1 | 9/1999 |
| WO | WO-9947525 A1 * 9/1999 | .............. A61P 13/00 |
| WO | 2000078712 | 12/2000 |
| WO | 2004050607 A1 | 6/2004 |
| WO | 2006056282 A1 | 6/2006 |

OTHER PUBLICATIONS

Extended European Search Report for European Patent Application 16180827.4 dated Jan. 23, 2017.
International Search Report for International Patent Application No. PCT/EP2017/068345 dated Aug. 31, 2017.
Hitomi Suzuki et al; "A Facile Synthetic Route to Some Arylmalonitriles"; Chemistry Letters, 1983, vol. 12, No. 4 pp. 589-590.
Schnyder A et al., A Convenient Protocol for the Synthesis of Hindered Aryl Malononitriles, No. 18, Synlett 2006, p. 3167-3169.

* cited by examiner

*Primary Examiner* — Matthew P Coughlin
(74) *Attorney, Agent, or Firm* — BakerHostetler; Toni-Junell Herbert

(57) ABSTRACT

Process for the preparation of a compound of Formula (I):

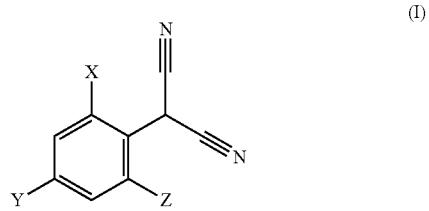

the process comprising the reaction of a compound of Formula (II) with malononitrile in the presence of a base and a palladium catalyst,

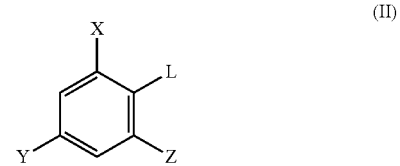

wherein X, Y and Z, independently of each other, represent fluoro, chloro or $C_{1-4}$alkyl; and L is a leaving group; with the proviso that 1 or 2 of X and Y are, independently of each other, fluoro or chloro.

19 Claims, No Drawings

PROCESS AND INTERMEDIATE

CROSS-REFERENCE TO RELATED APPLICATIONS

This application is a continuation of U.S. application Ser. No. 16/319,304, filed Jan. 18, 2019, which is a 371 National Stage application of International Application No. PCT/EP2017/068345, filed Jul. 20, 2017, which claims priority to European Application No. 16180827.4 filed Jul. 22, 2016, the entire contents of which applications are hereby incorporated by reference.

The present invention relates to a process for the preparation of certain phenyl acetic acid derivatives, to intermediate dinitrile compounds useful in the process for the preparation of certain phenyl acetic acid derivatives, and to a process for the preparation of the intermediate dinitrile compounds.

Phenyl acetic acid derivatives have been disclosed in WO 97/002243 and WO 2015/007640 as intermediates in the preparation of spiroheterocyclic pyrrolidine diones, which are useful for combating and controlling pests such as insect, acarine, mollusc and nematode pests. Improved processes for the preparation of phenyl acetic acid derivatives, in particular, halogenated (eg, mono- or dichlorinated) phenyl acetic acid derivatives, have subsequently been sought.

WO 00/78712 and WO 2004/050607 disclose the preparation of phenylmalonic acid dinitriles.

According to the present invention, there is provided a process for the preparation of a compound of Formula (I):

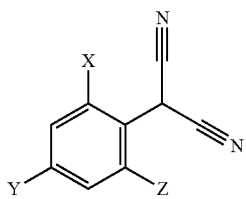
(I)

the process comprising the reaction of a compound of Formula (II) with malononitrile in the presence of a base and a palladium catalyst,

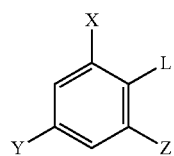
(II)

wherein

X, Y and Z, independently of each other, represent fluoro, chloro or $C_{1-4}$alkyl; and L is a leaving group;

with the proviso that 1 or 2 of X and Y are, independently of each other, fluoro or chloro.

According to a second aspect of the invention, there is provided a process for the preparation of a compound of Formula (III):

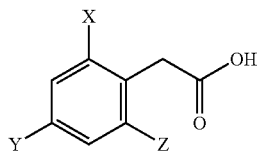
(III)

the process comprising the reaction of a compound of Formula (I) according to the invention with an acid (or a base) in the presence of water, and optionally a further diluent.

According to a third aspect of the invention, there is provided a compound of Formula (I):

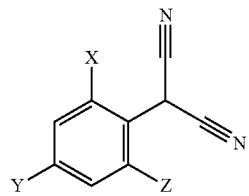
(I)

wherein

X, Y and Z, independently of each other, represent fluoro, chloro or $C_{1-4}$alkyl; and with the proviso that 1 or 2 of X and Y are, independently of each other, fluoro or chloro.

It has been found that the processes according to the invention result in high yielding syntheses of the compounds according to Formulae (I) and (Ill). Furthermore, the processes according to the invention may provide accelerated reaction rates. Additionally, the processes according to the invention are suitable for the large-scale preparation of compounds according to Formulae (I) and (Ill).

Compounds of Formula (III) may find utility in the so-called Ugi multi-component reaction (Ugi-MCR) which is a one-pot condensation of a carboxylic acid (eg, compound according to Formula (III)), another carbonyl-containing moiety, an isocyanide and an amine (eg, an alkylamine such as methyl amine), each of which may be introduced simultaneously or in any sequence to a reaction vessel to form a diamide compound (eg, see WO 2015/007640). Such diamide compounds may be ring-closed to yield a spirone compound (which may be derivatised with the addition of a latentiating group), such as those which are useful for combating and controlling pests such as insect, acarine, mollusc and nematode pests (eg, see WO 2010/066780).

Preferably, the process for the preparation of a compound of Formula (I), comprises steps (i) and (ii), wherein:

(i) malononitrile is reacted with base to form a malononitrile anion ([NCCHCN]$^-$); and (ii) the compound of Formula (II) is reacted with the malononitrile anion of step (i) in the presence of palladium catalyst to form a compound of Formula (I).

In the compounds of Formulae (I), (II) and (III) according to the invention, X, Y and Z independently of each other represent fluoro, chloro or $C_{1-4}$alkyl. Preferably, X, Y and Z independently of each other represent fluoro, chloro or methyl. More preferably, X, Y and Z independently of each other represent chloro or methyl. Most preferably, X is methyl, Y is chloro and Z is methyl.

In the compounds of Formula (II), Y is a leaving group. The leaving group may be selected from halogen, RS(O)$_2$O— wherein R is $C_{1-4}$alkyl, preferably methyl, $C_{1-4}$haloalkyl, preferably halomethyl or n-$C_4F_9$—, aryl, preferably phenyl, or phenyl substituted from one to three times by halogen, methyl or by halomethyl; and mono-, di- and tri-arylmethoxy. The aryl radicals of the mono-, di- and tri-arylmethoxy groups are preferably phenyl radicals, which may be substituted, for example, from one to three times by methyl, the substituents preferably being in the 2-, 4- and/or 6-positions of the phenyl ring. Examples of such leaving groups are methylsulfonyloxy (mesylate), trifluoromethylsulfonyloxy (triflate), p-tolylsulfonyloxy (tosylate), $CF_3(CF_2)_3S(O)_2O$— (nonaflate), diphenylmethoxy, di(methylphenyl)methoxy, triphenylmethoxy (trityl) and tri(methylphenyl)methoxy. Preferably, Y is a halogen, and most preferably bromo.

The diluents (eg, solvents, suspending agents) suitable for the preparation of a compound of Formula (I) according to the present invention include aliphatic, cycloaliphatic and aromatic hydrocarbons, for example pentane, hexane, petroleum ether, cyclohexane, methylcyclohexane, benzene, toluene or xylenes, aliphatic halohydrocarbons, for example, methylene chloride, chloroform, or di- or tetra-chloroethane, nitriles, for example acetonitrile, propionitrile or benzonitrile, ethers, for example diethyl ether, dibutyl ether, tert-butyl methyl ether, ethylene glycol dimethyl ether, ethylene glycol diethyl ether, diethylene glycol dimethyl ether, tetrahydrofuran or dioxane, alcohols, for example methanol, ethanol, propanol, butanol, ethylene glycol, diethylene glycol, ethylene glycol monomethyl or monoethyl ether or diethylene glycol monomethyl or monoethyl ether, ketones, for example acetone or methyl isobutyl ketone, esters or lactones, for example, ethyl or methyl acetate or valerolactone, N-substituted lactams, for example N-methyl-2-pyrrolidone (NMP or 1-methyl-2-pyrrolidone), amides, for example N,N-dimethylformamide (DMF) or dimethylacetamide (DMA), acyclic ureas, for example N,N'dimethylethyleneurea (DMI), sulfoxides, for example dimethyl sulfoxide (DMSO), or mixtures of such diluents. Water may also be used as a component of a biphasic mixture. Preferably, the process for the preparation of a compound of Formula (I) is carried out in the presence of a dipolar aprotic diluent, such as N,N-dimethylformamide, dimethyl sulfoxide, N-methyl-2-pyrrolidone, N,N-dimethylacetamide, N,N'-dimethylethyleneurea. N-methyl-2-pyrrolidone is most preferred.

The process for the preparation of compounds of Formula (I) generally proceeds via two steps, firstly involving the generation of a malononitrile anion generated by reacting malononitrile with a base (eg, hydroxide), and, secondly, reaction of the malononitrile anion (in situ) with the compound of Formula (II) to carbon couple the anion to the phenyl ring of the compound of Formula (II), with loss of the leaving group L (eg, bromo). Preferably, the process is performed at a temperature of 50 to 200° C., more preferably at 80 to 170° C., and most preferably at 110 to 150° C. In some embodiments, increased pressure may be applied to the reaction conditions.

For the preparation of the malononitrile anion, inorganic or organic bases may be used. In particular, alkali metal hydroxides or mixtures of alkali metal hydroxides, alkali metal alkoxides or carbonates (eg, potassium carbonate, sodium carbonate, calcium carbonate, cesium carbonate) may be used. Hydroxides of alkali metals or mixtures of hydroxides of alkali metals are preferred. Sodium and potassium hydroxide (and mixtures thereof) are preferred, and especially sodium hydroxide. Preferably, the base is used from a molar equivalent to an excess of 10 equivalents in relation to malononitrile. More preferably, the base is used in amounts of 2 to 5 equivalents, or 2 to 4 equivalents in relation to malononitrile.

The process for the preparation of a compound of Formula (I) is carried out in the presence of a palladium catalyst, ie, to catalyse the carbon coupling reaction of the malononitrile anion. The palladium catalysts which may be useful for the carbon coupling anion are generally palladium (II) or palladium (0) complexes, for example palladium (II) dihalides, palladium (II) acetate, palladium (II) sulfate, bis(triphenylphosphine) palladium (II) dichloride, bis-(tricyclopentylphosphine) palladium (II) dichloride, bis(tricyclohexylphosphine) palladium (II) dichloride, bis(dibenzylideneacetone) palladium (0) or tetrakis(triphenylphosphine) palladium (0). Preferably, the palladium catalyst is prepared in situ from palladium (II) or palladium (0) compounds by complexing with phosphine ligands.

Examples of such ligands, include trimethylphosphine, triethylphosphine, tris(tert-butyl)phosphine, tricyclopentylphosphine, tricyclohexylphosphine ($PCy_3$), tri(methylcyclohexyl)phosphine, methyl(tetramethylene)phosphine, tert-butyl(pentamethylene) phosphine, triphenylphosphine ($PPh_3$), tri(methylphenyl)phosphine, 1,2-diphenylphosphinecyclohexane, 1,2-diphenylphosphinecyclopentane, 2,2'-(diphenylphosphine)-biphenyl, 1,2-bis(diphenylphosphine)ethane, 1,3-bis(diphenylphosphine) propane, 1,4-bis(diphenylphosphine)butane, 3,4-bis(diphenylphosphine) pyrrolidine, 2,2'-(diphenylphosphine)-bisnaphthyl (Binap), 1,1'-bis(diphenylphosphine)-ferrocene, 1,1'-bis (di-tert-butylphosphine) ferrocene, diphenyl ether bisdiphenylphosphine

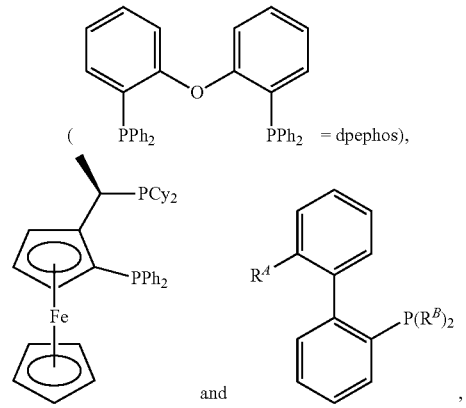

wherein $R^A$ is hydrogen or dimethylamino, and $R^B$ is cyclohexyl or tert-butyl.

The palladium catalyst used in the preparation of a compound of Formula (I) is present in an effective catalytic amount, which may for example be at a molar ratio to the compound of Formula (II) of 1:100 to 1:500, and preferably 1:200 to 1:400.

The process for the preparation of compounds of Formula (III) relates to the acid hydrolysis of the nitrile groups of the compounds of Formula (I). An inorganic acid may be used. Preferably, the acid is hydrochloric acid or sulphuric acid, and more preferably sulphuric acid. Additionally, preferably, the acid is present in at least two molar equivalents to the compound of Formula (I). More preferably, the acid is present at 2 to 5 molar equivalents, and even more preferably 3 to 4 molar equivalents to the compound of Formula (I).

The process for the preparation of a compound of Formula (III) is carried out in the presence of water (preferably, at least 4 molar equivalents) and optionally a further diluent. In some embodiments, the acid will be present in aqueous form and the compound of Formula (I) as a solution in a hydrocarbon solvent, such as benzene, toluene, xylene, mesitylene, and preferably, toluene or xylene. The reaction may be carried out in a water/toluene or water/xylene azeotrope under distillation conditions to reduce toluene/xylene and enrich water content in the reaction mixture.

Preferably, the process for the preparation of a compound according to Formula (III) is performed at a temperature of 100 to 180° C., more preferably at 110 to 160° C., and most preferably at 120 to 155° C. In some embodiments, increased pressure may be applied to the reaction conditions.

Compounds of Formula (II) may be prepared from methods known in the literature, eg, WO 2010/102761 and WO 2006/084663.

Scheme 1 General reaction scheme of a process for the preparation of the compounds of Formula (I) and (III)

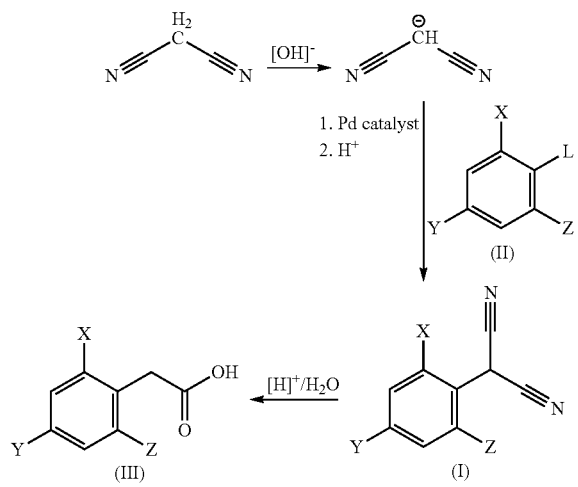

TABLE 1

This table discloses compounds 1.1 to 1.6 according to Formula (I) of the present invention, wherein X, Y and Z are defined in the following table

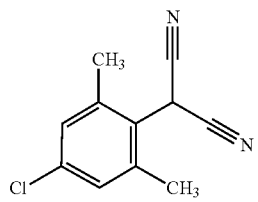

| Compound no. | X | Y | Z |
|---|---|---|---|
| 1.1 | CH$_3$ | F | CH$_3$ |
| 1.2 | CH$_3$ | Cl | CH$_3$ |
| 1.3 | F | CH$_3$ | CH$_3$ |
| 1.4 | Cl | CH$_3$ | CH$_3$ |

TABLE 1-continued

| 1.5 | F | F | CH$_3$ |
| 1.6 | Cl | Cl | CH$_3$ |

Preferably, the compound of Formula (I) is 2-(4-chloro-2,6-dimethyl-phenyl)propanedinitrile.

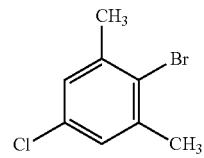

Preferably, the compound of Formula (II) is 2-bromo-5-chloro-1,3-dimethyl-benzene.

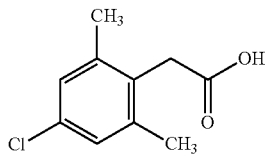

Preferably, the compound of Formula (III) is 2-(4-chloro-2,6-dimethyl-phenyl)acetic acid.

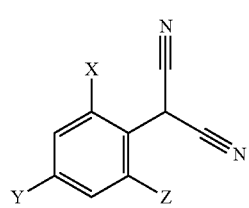

The processes of the present invention may be used in the preparation of any of the compounds of Formulae (IV), (VII) or (VIII) according to steps (i) to (v) as follows (and with reference in particular to the disclosure and examples of WO 2009/049851, WO 2010/066780 and WO 2015/007640):

(i) the preparation of a compound of Formula (I)

(I)

comprising the reaction of a compound of Formula (II) with malononitrile in the presence of a base and a palladium catalyst,

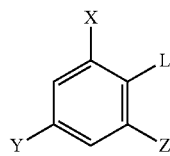

(II)

wherein X, Y and Z, independently of each other, represent fluoro, chloro or $C_{1-4}$alkyl with the proviso that 1 or 2 of X and Y are, independently of each other, fluoro or chloro, and L is a leaving group;

(ii) reacting the compound of Formula (I) with an acid (or a base) in the presence of water, and optionally a further diluent, to form a compound of Formula (III),

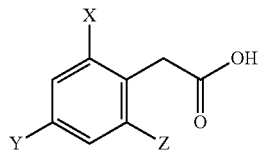

(III)

wherein X, Y and Z are as defined for step (i);

(iii) the preparation of a compound of Formula (IV)

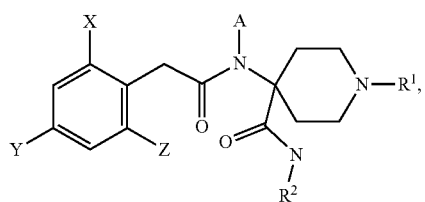

(IV)

wherein A is $C_{1-4}$alkyl (preferably methyl), $R^1$ is $C_{1-4}$alkoxy (preferably methoxy), $R^2$ is phenyl or phenyl substituted by one or more substituents selected from the group consisting of $C_{1-4}$alkyl, $C_{1-4}$haloalkyl, $C_{1-4}$alkoxy, halogen and nitro, and X, Y and Z are as defined for step (i), comprising reacting a compound of Formula (III) with a compound of Formula (V),

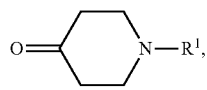

(V)

a compound of Formula (VI)

(VI)

and an amine of formula A-NH$_2$;

(iv) the preparation of a compound of Formula (VII)

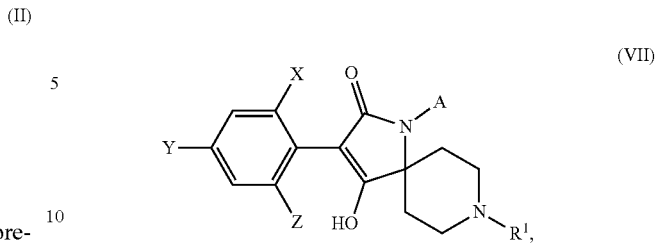

(VII)

wherein X, Y, Z, A and $R^1$ are as defined for step (iii), comprising treating a compound of Formula (IV) with a suitable base in an appropriate solvent (or diluent); and (v) the preparation of a compound of Formula (VIII)

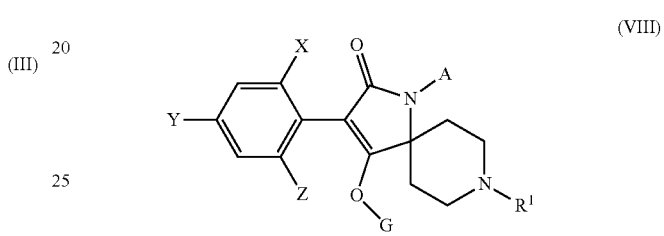

(VIII)

wherein X, Y, Z, A and $R^1$ are as defined for step (iv) and G is a latentiating group C(O)R wherein R is $C_{1-4}$alkoxy (preferably ethoxy), comprising reacting a compound of Formula (VII) with an acid halide, in particular an acid halide of the formula RC(O)Cl, preferably in the presence of at least one equivalent of a base.

It is understood that the preferred embodiments for X, Y and Z in accordance with the present invention may apply equally to steps (i) to (v).

PREPARATION EXAMPLES

The Examples which follow serve to illustrate the present invention.

Compounds of Formula (I) are prepared using malononitrile (N≡C—CH$_2$—C≡N), which is commercially available. Other reagents used in accordance with the preparation examples are also commercially available. 2-Bromo-5-chloro-1,3-dimethyl-benzene and 2-iodo-5-chloro-1,3-dimethyl-benzene may be prepared according to literature methods as described in, eg, WO 2006/084663.

Example 1

Preparation of 2-(4-chloro-2,6-dimethyl-phenyl)propanedinitrile

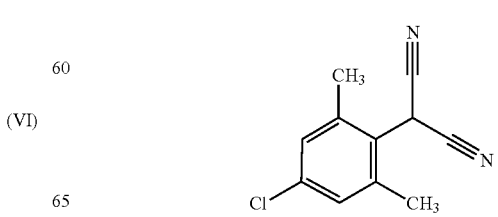

To a 400 mL vessel equipped with a mechanical stirrer, thermometer, distillation head and dropping funnel, solid sodium hydroxide (10.9 g, 0.27 mol, microprills with 0.5-1 mm diameter) is charged under an inert atmosphere.

1-Methyl-2-pyrrolidone (NMP, 137 g) is added to the vessel in one portion through the dropping funnel and the reaction mixture cooled to 10-15° C. while stirring. A solution of malononitrile (N≡C—CH$_2$—C≡N) (6.6 g, 0.10 mol) in NMP (8.9 g) is added through the dropping funnel over 10-15 minutes maintaining the temperature at 10-15° C. The reaction mixture is then heated to 100° C. and a vacuum (30 mbar) applied, upon which solvent (40 g) is distilled off.

2-Bromo-5-chloro-1,3-dimethyl-benzene (20 g, 0.089 mol) is then added through the dropping funnel over 5-10 minutes, whilst maintaining the temperature at 100-110° C. A mixture containing palladium (II) chloride (0.19 g, solution in conc. hydrochloric acid, assay 20% Pd, 0.36 mmol), triphenylphosphine (0.45 g, 1.6 mmol) and NMP (18 g) is then added through the dropping funnel over a 5-10 minute period. The temperature is allowed to rise to 124° C. and the reaction mixture stirred at this temperature for 2-3 hours. Conversion is monitored by pulling samples and subsequent HPLC analysis.

When conversion is complete, a vacuum (20-40 mbar) is applied and solvent (90 g) is distilled off. The resulting residue is cooled below 100° C. and water (95 g) is added. After cooling to room temperature, the resulting mixture is filtered through hyflo (Hyflo® SuperCel® diatomaceous earth, ca. 10 g) and the filter cake washed with water (20 g). To the combined filtrates, hydrochloric acid (20.6 g, assay 32%, 0.18 mol) is added to adjust the pH from 13.3 to 2.7.

The resulting mixture is extracted with tert-butyl-methyl ether (2×110 g). The organic phases are washed with water (2×50 g) and the combined organic phases evaporated to dryness. The resulting solid residue is recrystallized from iso-propanol (63 g) and the resulting crystals filtered, washed with cold iso-propanol (5 g) and dried under vacuum to yield 2-(4-chloro-2,6-dimethyl-phenyl)propanedinitrile (melting point (m.p.) 145-147° C.).

$^1$H-NMR (CDCl$_3$) δ (ppm): 2.6 (s), 6H; 5.3 (s), 1H; 7.2 (s), 2H.

Example 2

Preparation of
2-(4-chloro-2,6-dimethyl-phenyl)propanedinitrile

To a 1 litre vessel equipped with mechanical stirrer, thermometer, distillation head, joints for dosing liquids by pump, and gas inlet tube (below surface) solid sodium hydroxide (87.1 g, 2.18 mol, microprills with 0.5-1 mm diameter) is charged under an inert atmosphere.

1-Methyl-2-pyrrolidone (NMP, 682 g) is added in one portion while stirring and the resulting mixture cooled to 10-14° C. A solution of malononitrile (49.2 g, 0.736 mol) in NMP (65 g) is added via a pump over 15-20 minutes while maintaining the temperature at 10-14° C. A vacuum (30 mbar) is applied and the resulting mixture is heated to 100-110° C. until solvent (198 g) is distilled off. The mixture is then heated to 130° C. and a stream of nitrogen (4.5 litres/hour) is passed through.

A mixture containing palladium (II) chloride (1.15 g, solution in conc. hydrochloric acid; assay 20% Pd, 2.17 mmol), triphenylphosphine (1.50 g; 5.72 mmol) and NMP (147 g) is dosed in via a pump within a 70 minute period. After 20 minutes feeding the aforementioned mixture, 2-bromo-5-chloro-1,3-dimethyl-benzene (160 g, 0.715 mol) is also dosed in in parallel via a pump within 50 minutes.

After both additions have been completed, the reaction mixture is maintained at 130° C. for a further 3 hours. A vacuum (20-30 mbar) is applied and solvent (603 g) is distilled off. The resulting residue is cooled below 100° C. and water (450 g) is added. The resulting mixture is cooled to 40° C. Hydrochloric acid (180 g, assay 32%, 1.58 mol) is added in order to reduce the pH from 13.1 to 2.0. Toluene (535 g) is added for extraction of the product.

The two phase mixture is filtered through hyflo (ca. 15 g) and the filter-cake washed with toluene (45 g). The combined filtrates are transferred to a separation funnel, the aqueous phase separated and the organic phase washed with water (400 g). All aqueous phases are re-extracted with toluene (360 g) and all organic phases combined and evaporated to dryness. The solid residue is recrystallized with iso-propanol (650 g). The resulting crystals are filtered and washed with iso-propanol (55 g) and dried under vacuum to yield 2-(4-chloro-2,6-dimethyl-phenyl)propanedinitrile (m.p. 145-147° C.).

Example 3

Preparation of
2-(4-chloro-2,6-dimethyl-phenyl)propanedinitrile

To a 250 mL vessel equipped with a mechanical stirrer, thermometer, distillation head and dropping funnel, solid sodium hydroxide (3.9 g, 0.10 mol, microprills with 0.5-1 mm diameter) is charged under an inert atmosphere. 1-Methyl-2-pyrrolidone (NMP, 68 g) is added to the vessel in one portion through the dropping funnel and the reaction mixture cooled to 10-15° C. while stirring. A solution of malononitrile (N≡C—CH$_2$—C≡N) (2.27 g, 0.034 mol) in NMP (2.7 g) is added through the dropping funnel over 5 minutes maintaining the temperature at 10-15° C. The reaction mixture is then heated to 100° C. and a vacuum (30 mbar) applied, upon which solvent (32 g) is distilled off. The mixture is then heated to 130° C. and a stream of nitrogen is passed through.

2-Iodo-5-chloro-1,3-dimethyl-benzene (9.0 g, 95% purity, 0.032 mol) is then added through the dropping funnel over 5 minutes at 130° C. A mixture containing palladium (II) chloride (0.150 g, solution in conc. hydrochloric acid, assay 20% Pd, 0.281 mmol), triphenylphosphine (0.186 g, 0.709 mmol) and NMP (13.7 g) is then added through the dropping funnel over a 2-minute period. The temperature is allowed to rise to 130° C. and the reaction mixture stirred at this temperature for 80 min. Conversion is monitored by pulling samples and subsequent HPLC analysis. A second portion of a mixture containing palladium (II) chloride (0.103 g, solution in conc. hydrochloric acid, assay 20% Pd, 0.194 mmol), triphenylphosphine (0.132 g, 0.504 mmol) and NMP (9.76 g) is then added through the dropping funnel over a 2-minute period and the reaction mixture stirred at 130° C. for 40 min.

When conversion is complete, a vacuum (20-40 mbar) is applied and solvent (38 g) is distilled off. The resulting residue is cooled to 80° C. and water (30 g) is added. After cooling to room temperature, the resulting mixture is filtered through a filter paper and the filter cake washed with water (10 g). To the combined filtrates, hydrochloric acid (9.6 g, assay 32%, 0.084 mol) is added to adjust the pH from 13.3 to 1.3.

The resulting mixture is extracted with toluene (50 g). The organic phase is washed with water (2×20 g) and evaporated to dryness. The resulting solid residue is recrystallized from 1-pentanol (17 g) and the resulting crystals filtered, washed with 1-pentanol (4 g) and dried under vacuum to yield 2-(4-chloro-2,6-dimethyl-phenyl)propanedinitrile (melting point (m.p.) 145-147° C.).

Example 4

Preparation of 2-(4-chloro-2,6-dimethyl-phenyl)acetic acid

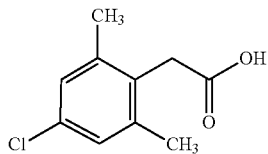

To a 500 mL reaction vessel equipped with thermometer, mechanical stirrer, distillation head with water trap and dropping funnel is added water (100 g) and concentrated sulphuric acid (assay 98%, 179 g, 1.79 mol).

The mixture is stirred and heated to 120-130° C., and a solution of 2-(4-chloro-2,6-dimethyl-phenyl)propanedinitrile (assay 92.8%, 91.5 g, 0.415 mol) in toluene (1070 g) dosed in over 2 hours. The solvent (toluene/water azeotrope) is distilled off, and the water separated in the water trap is transferred back to the reaction mixture. After all of the organic solvent has been distilled off, the resulting reaction mass is heated to 140° C. for an additional 4 hours. Conversion is monitored by sampling and HPLC-analysis.

After complete conversion, the reaction mass is cooled to 60° C. and introduced into well-agitated water (900 g). The resulting mixture, a suspension, is cooled to 25° C. and filtered. The filter-cake, the desired product, is washed with water (2×220 g) and dried under vacuum. Crude 2-(4-chloro-2,6-dimethyl-phenyl)acetic acid is obtained, which is recrystallized from toluene (608 g) affording pure 2-(4-chloro-2,6-dimethyl-phenyl)acetic acid (m.p. 187-189° C.).

$^1$H-NMR (CDCl$_3$) δ(ppm): 2.2 (s), 6H; 3.6 (s), 2H; 7.0 (s), 2H.

Example 5

Preparation of 2-(4-chloro-2,6-dimethyl-phenyl)acetic acid

To a 300 mL reaction vessel equipped with thermometer, mechanical stirrer and reflux condenser is added water (41 g) and concentrated sulphuric acid (assay 98%, 72 g, 0.72 mol). The mixture is stirred and heated to 140° C.

Solid 2-(4-chloro-2,6-dimethyl-phenyl)propanedinitrile (assay 98.4%, 50 g, 0.24 mol) is added over a 70 minute period in 10 equal portions while maintaining the temperature at 140° C. The reaction mixture is stirred at 140° C. for another 2-3 hours and conversion is controlled by sampling and HPLC-analysis. When conversion is complete, the resulting mixture, a suspension, is cooled to room temperature. Water (100 g) is added and the suspension is filtered. The filter-cake, the desired product, is washed with water (2×50 g) and dried under vacuum. Crude 2-(4-chloro-2,6-dimethyl-phenyl)acetic acid is obtained.

The invention claimed is:
1. A process, comprising:
reacting a compound of Formula (I)

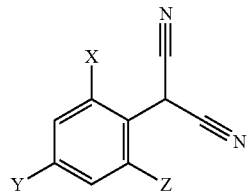

wherein
X, Y and Z, independently of each other, represent fluoro, chloro or C$_{1-4}$ alkyl, and with the proviso that 1 or 2 of X and Y are, independently of each other, fluoro or chloro;
with an acid in the presence of water, and a hydrocarbon solvent to form a compound of Formula (III)

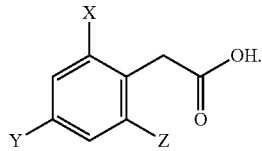

2. The process of claim 1, wherein the hydrocarbon solvent is benzene.
3. The process of claim 1, wherein the hydrocarbon solvent is mesitylene.
4. The process of claim 1, wherein the hydrocarbon solvent is xylene.
5. The process of claim 1, wherein the hydrocarbon solvent is toluene.
6. The process of claim 1, wherein the solvent is an aromatic hydrocarbon solvent.
7. The process of claim 6, wherein the reacting of the compound of Formula (I) to form the compound of Formula (III) is under distillation conditions.
8. The process of claim 6, wherein the water and aromatic hydrocarbon solvent form an azeotrope.
9. The process of claim 6, wherein the reacting of the compound of Formula (I) to form the compound of Formula (III) is at a temperature of 120 to 155° C.
10. The process of claim 6, wherein the reacting of the compound of Formula (I) to form the compound of Formula (III) is at increased pressure.
11. The process of claim 1, wherein X, Y, and Z are defined as follows:

| X | Y | Z |
|---|---|---|
| CH$_3$ | F | CH$_3$ |
| CH$_3$ | Cl | CH$_3$ |
| F | CH$_3$ | CH$_3$ |
| Cl | CH$_3$ | CH$_3$ |
| F | F | CH$_3$ |
| Cl | Cl | CH$_3$. |

12. The process of claim 11, wherein X is CH$_3$, Y is Cl, and Z is CH$_3$.

13. A process, comprising:
preparing a reaction vessel with solid sodium hydroxide and an inert atmosphere;
adding a dipolar aprotic solvent to the reaction vessel;
cooling the reaction vessel containing the dipolar aprotic solvent and solid sodium hydroxide and adding malononitrile to the reaction vessel;
adding 2-bromo-5-chloro-1,3-dimethyl-benzene to the reaction vessel; and
adding a mixture containing palladium (II) and a second dipolar aprotic solvent to the reaction vessel and forming 2-(4-chloro-2,6-dimethyl-phenyl)propanedinitrile.

14. The process of claim 13, wherein cooling is below room-temperature.

15. The process of claim 14, further comprising distilling off the dipolar aprotic solvent after cooling.

16. The process of claim 15, wherein the dipolar aprotic solvent and the second dipolar aprotic solvent are selected from at least one of N,N-dimethylformamide, dimethyl sulfoxide, N-methyl-2-pyrrolidone, N,N-dimethylacetamide, and N,N'-dimethylethyleneurea.

17. The process of claim 16, wherein the dipolar aprotic solvent and the second dipolar aprotic solvent are N-methyl-2-pyrrolidone and the temperature of the reaction vessel is between 80 to 170° C. when the reaction vessel contains 2-bromo-5-chloro-1,3-dimethyl-benzene and the palladium (II) catalyst.

18. The process of claim 1, further comprising reacting the compound of Formula (III) with a compound of Formula (V),

(V)

wherein $R^1$ is $C_{1-4}$ alkoxy, a compound of formula (VI),

(VI)

wherein $R^2$ is phenyl or phenyl substituted by one or more substituents selected from the group consisting of $C_{1-4}$ alkyl, $C_{1-4}$ haloalkyl, $C_{1-4}$ alkoxy, halogen and nitro, and an amine of formula A-NH$_2$, wherein A is $C_{1-4}$ alkyl, to form a compound of Formula (IV),

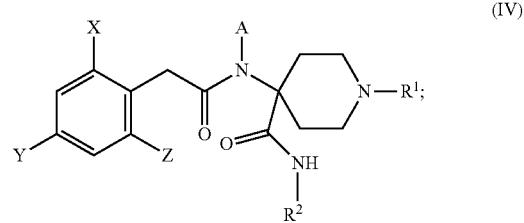

(IV)

reacting the compound of formula (IV) with a base to form a compound of Formula (VII),

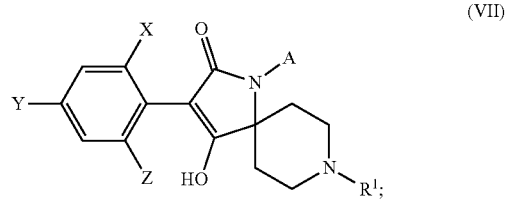

(VII)

and reacting the compound of Formula (VII) with an acid halide to form a compound of Formula (VIII),

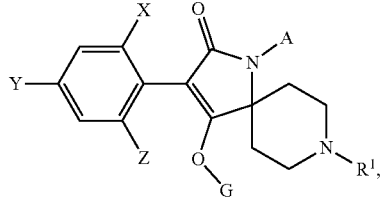

(VIII)

wherein G is C(O)R, and R is $C_{1-4}$ alkoxy.

19. The process of claim 18, wherein:
X is CH$_3$, Y is Cl, and Z is CH$_3$;
A is methyl;
$R^1$ is methoxy; and
R is ethoxy.

* * * * *